May 7, 1940. J. F. STYER Plant Pat. 391
CHRYSANTHEMUM PLANT
Filed June 23, 1939
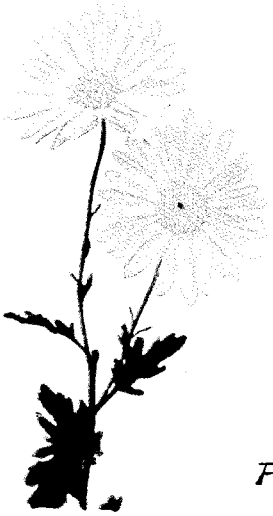
Fig I
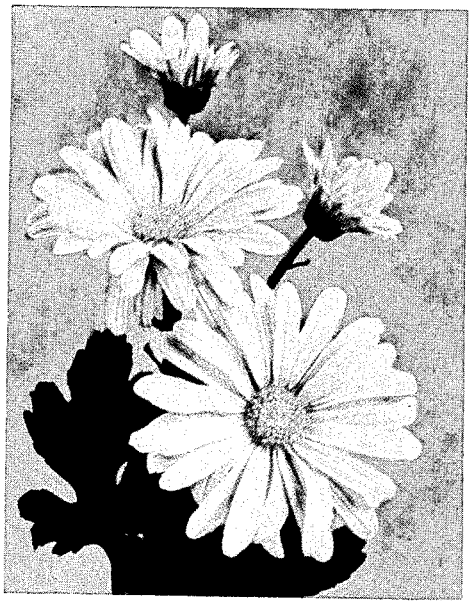
Fig II
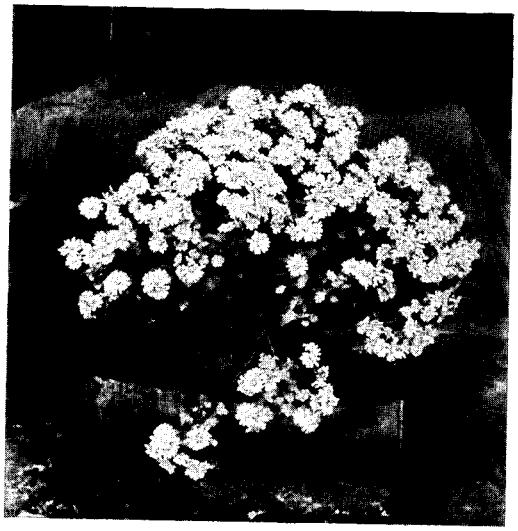
Fig III
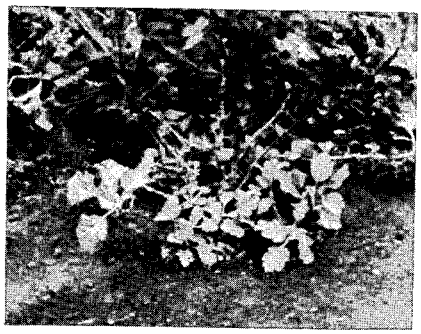
Fig IV
INVENTOR
John Franklin Styer
By Oroille M. Kile
Plant Patent Agent Patented May 7, 1940 Plant Pat. 391

UNITED STATES PATENT OFFICE

391

CHRYSANTHEMUM PLANT

John Franklin Styer, Concordville, Pa.

Application June 23, 1939, Serial No. 280,869

1 Claim. (Cl. 47—60)

My invention relates to improvements in hardy perennial chrysanthemums and consists of a new and improved variety, differing radically in plant form and growth features from previously known chrysanthemums, with the single exception of the variety Astrid (and descendants) which is the parent of the present variety, from which it differs in several important respects, particularly in color. The color of the present variety lies in the yellow range while the parent variety color is in the pale pink range. Also the color of the new variety fades much less than that of its parent.

This new variety was obtained by the inventor from seed produced by self-fertilization of the variety Astrid, which is believed to be a hybrid of *Chrysanthemum articum* with an unknown garden chrysanthemum, and which originated on my property in Concordville. I planted the seeds of Astrid from which a large number of seedlings were produced. In the mass these seedlings exhibited certain variations in such numbers as to indicate them to be the second generation of a true hybrid. This new variety was selected from these seedlings, was reproduced asexually, and retains its distinguishing characteristics.

The fundamental improvement which distinguishes this new class of chrysanthemums is found in the plant and crown growth. The crown produces numerous underground stems which assure the winter-hardiness of the variety and which are capable of producing new plants which will, under conditions to be described, bloom normally in the spring. The plants of this variety may be lifted in mid-winter and divided, and plants so made may be grown indoors producing normal flowers of dependable quantity and quality about the month of May, on stems approximately 16 inches in height. This feature is inherent in the race of hybrid chrysanthemums of which this new variety is a member and especially serves to set this variety apart from chrysanthemums of previously known types, in which the feature was at best sporadic and abnormal.

The plant of this variety is exceptionally vigorous and grows into a perfect compact mound-shape without shearing or pinching. It is extremely hardy as a result of the vigorous and early crown growth, and is perfectly winter-hardy at Concordville, Pennsylvania.

The accompanying illustrations show different phases of this plant as follows: Fig. I, typical fall flowers; Fig. II, typical spring flowers; Fig. III, the plant as it appears in the fall; and Fig. IV, the crown growth as it appears in the fall.

In the following detailed description of this new variety of chrysanthemum, color plate references indicate Ridgway's Color Standards and Nomenclature. Where no plate numbers are given the ordinary dictionary term is intended.

*The plant*

Growth: Approximately mound-shaped. Dense, side branches filling in space close to ground. Consists of one to several stems from the ground, branching to produce 8 to 20 main stems which are mostly spreading. These branch again from 14 to 20 inches from the base, producing 3 to 8 sprays each.

*Sprays.*—Each spray produces usually 6 to 20 flowers on stems 2 to 4 inches long.

*Size.*—Average height of one-year plant is 30 inches; width, 50 inches.

*Crown.*—During the growing season the crown is extended by numerous underground stems 1 to 4 inches in length which turn upward and bear leafy tips ½ to 2 inches above the surface, the crown thus becoming 7 to 10 inches wide.

Foliage:

*Leaf blade.*—Usually 2 to 2½ inches wide by 2¼ to 3 inches long. Has five main lobes between which the leaf is cut ½ to 1 inch deep, the margin of each lobe being moderately toothed. Petiole—⅞ to 1 inch long.

*Color.*—Below, Elm Green (Plate XVII); above, Light Hellebore Green (Plate XVII).

*Texture.*—Heavy.

Stems: Light Elm Green (Plate XVII) on the younger stems. Older stems frequently have a bronzed or reddish tinge.

*Size.*—Heavy and thick.

Blooming: Fall season begins from October 8 to to 15 in my gardens.

*The flower*

Blossom:

*Size.*—Usually 2 to 2¾ inches across. Spring flowers are slightly larger.

*Form.*—Single or irregularly double row of 30 to 40 ray flowers surrounding a raised conical center which is ⅝ to ¾ inches across.

*Ray flowers.*—Size—one-fourth to $\frac{5}{16}$ inch wide by ⅞ to 1¼ inches long. Spring flowers have slightly larger ray flowers. Shape—inclined to be oval in shape and blunt at the end. Color in fall—Straw Yellow (Plate XVI) to Mustard Yellow (Plate XVI), sometimes slightly suffused with pink. Color in spring—varies from Amber Yellow (Plate XVI) to Empire Yellow (Plate IV), fading to Straw Yellow (Plate XVI). The bud is Light Cadmium (Plate IV) with traces of Raw Sienna (Plate III) at its base.

*Cushion.*—The cushion or center is cone shaped and composed of many pollen-bearing yellow florets arranged in standard concentric pattern of Compositae.

*Florets.*—Size—center florets are slightly more than ¼ inch long with pistil extending almost an equal length beyond. Color—Wax Yellow (Plate XVI).

Having thus disclosed my invention, I claim:

A new and distinct variety of perennial chrysanthemum substantially as shown and described, characterized particularly by its vigor and hardiness; its dense and compact mound shape; its unusual crown growth which enables it to normally produce flowers in the spring as well as in the fall; and its Straw Yellow to Empire Yellow blossoms differing in size and color in the spring and fall seasons.

JOHN FRANKLIN STYER.